United States Patent [19]

Nacci née Tagliaferri et al.

[11] Patent Number: 5,084,029
[45] Date of Patent: Jan. 28, 1992

[54] SYRINGE WHICH AUTOMATICALLY MAKE THE HYPODERMIC NEEDLE HARMLESS AFTER USE

[76] Inventors: Carla Nacci née Tagliaferri; Gaetano Nacci, both of Via delle Fonti, 17 - 50012 Bagno A Ripoli (Prov. of Florence), Italy

[21] Appl. No.: 543,816
[22] PCT Filed: Dec. 6, 1989
[86] PCT No.: PCT/EP89/01499
  § 371 Date: Jul. 17, 1990
  § 102(e) Date: Jul. 17, 1990
[87] PCT Pub. No.: WO90/06146
  PCT Pub. Date: Jun. 14, 1990

[30] Foreign Application Priority Data
  Dec. 7, 1988 [IT] Italy .................. 9543 A/88

[51] Int. Cl.⁵ .............................. A61M 5/00
[52] U.S. Cl. ..................... 604/195; 604/198
[58] Field of Search .......... 604/195, 198, 187, 110, 604/218

[56] References Cited

U.S. PATENT DOCUMENTS

| | | |
|---|---|---|
| 4,747,830 | 5/1988 | Gloyer et al. |
| 4,747,831 | 5/1988 | Kulli |
| 4,838,869 | 6/1989 | Allard ................. 604/195 |
| 4,874,382 | 10/1989 | Lindemann et al. ....... 604/195 |
| 4,955,870 | 9/1990 | Ridderheim et al. ...... 604/195 |

FOREIGN PATENT DOCUMENTS

| | | |
|---|---|---|
| 14189/88 | 10/1988 | Australia |
| 0282097 | 3/1988 | European Pat. Off. |
| WO89/00435 | 1/1989 | PCT Int'l Appl. |
| WO89/09075 | 10/1989 | PCT Int'l Appl. |

*Primary Examiner*—John D. Yasko

[57] ABSTRACT

The danger of hypodermic syringes is neutralized and they are made monouse by an arrangement including a needle (a), which shall be referred to as the perforated stiletto. This needle is provided with a female hook (k) and a cylindrical container (m), inserted coaxially in the piston rod (v) of the syringe. The cylindrical container can receive the perforated needle (a) by interacting with a male hooking pawl (n) and its support structure (o) and a cylindrical helicoidal pull string (q).

11 Claims, 3 Drawing Sheets

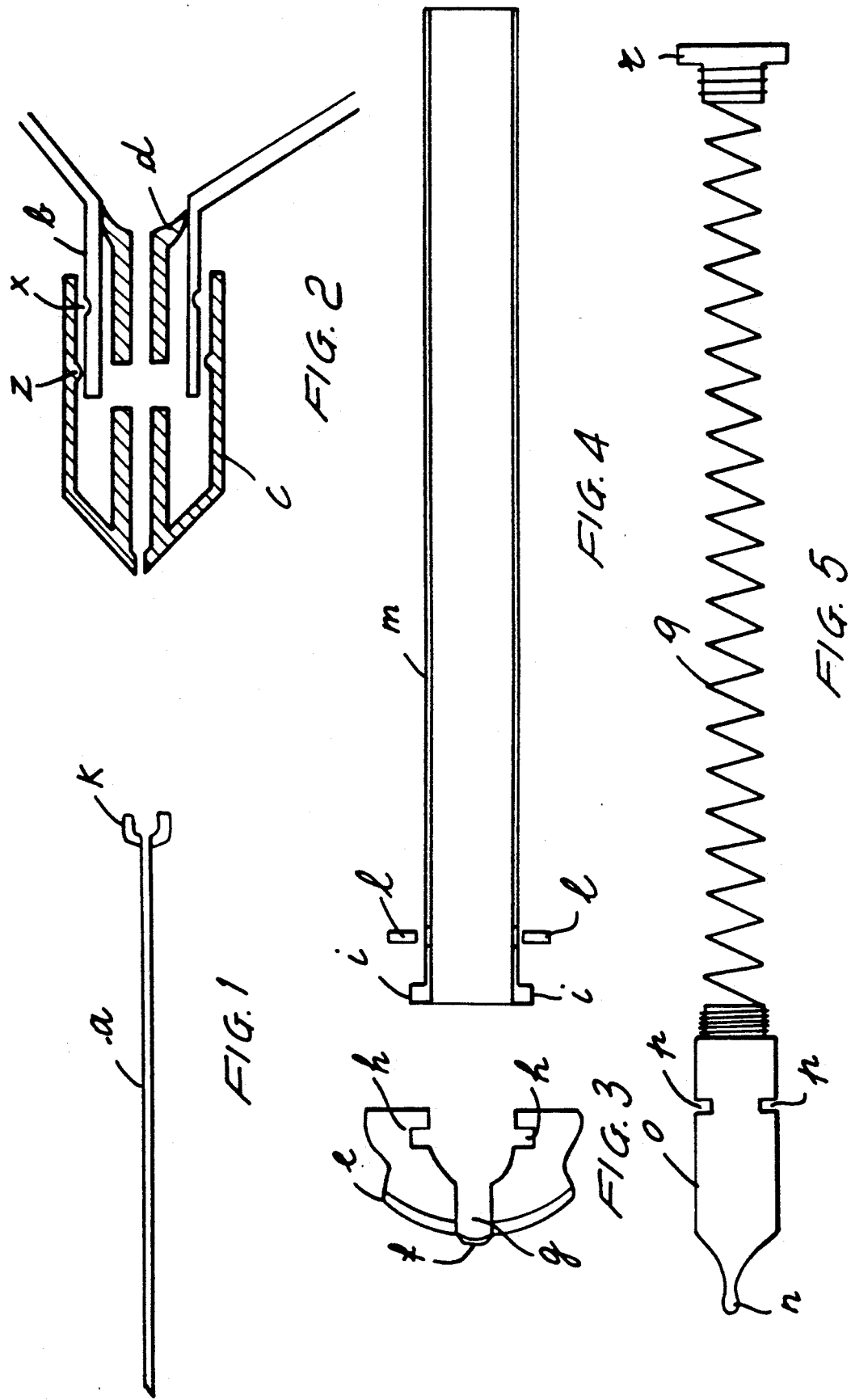

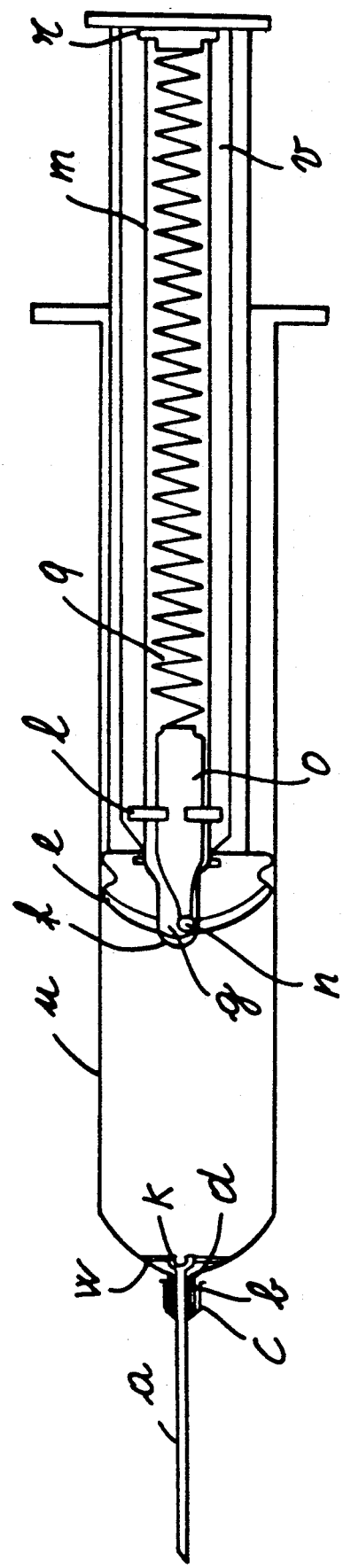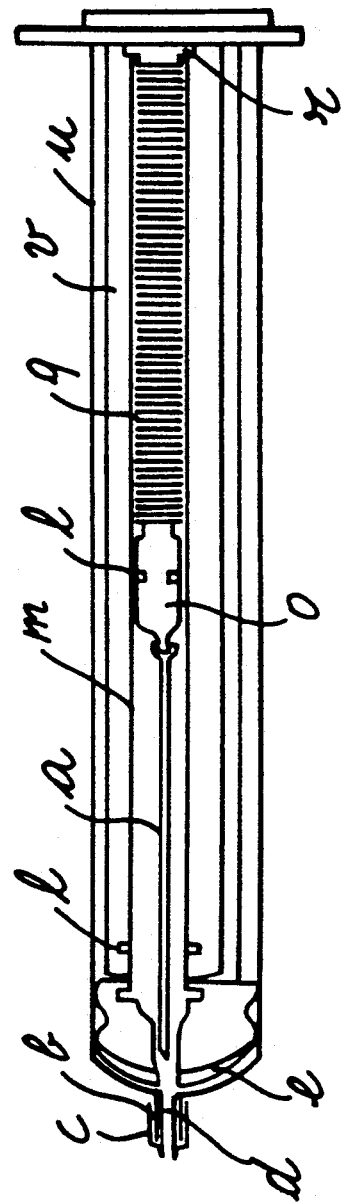
FIG. 6
FIG. 7

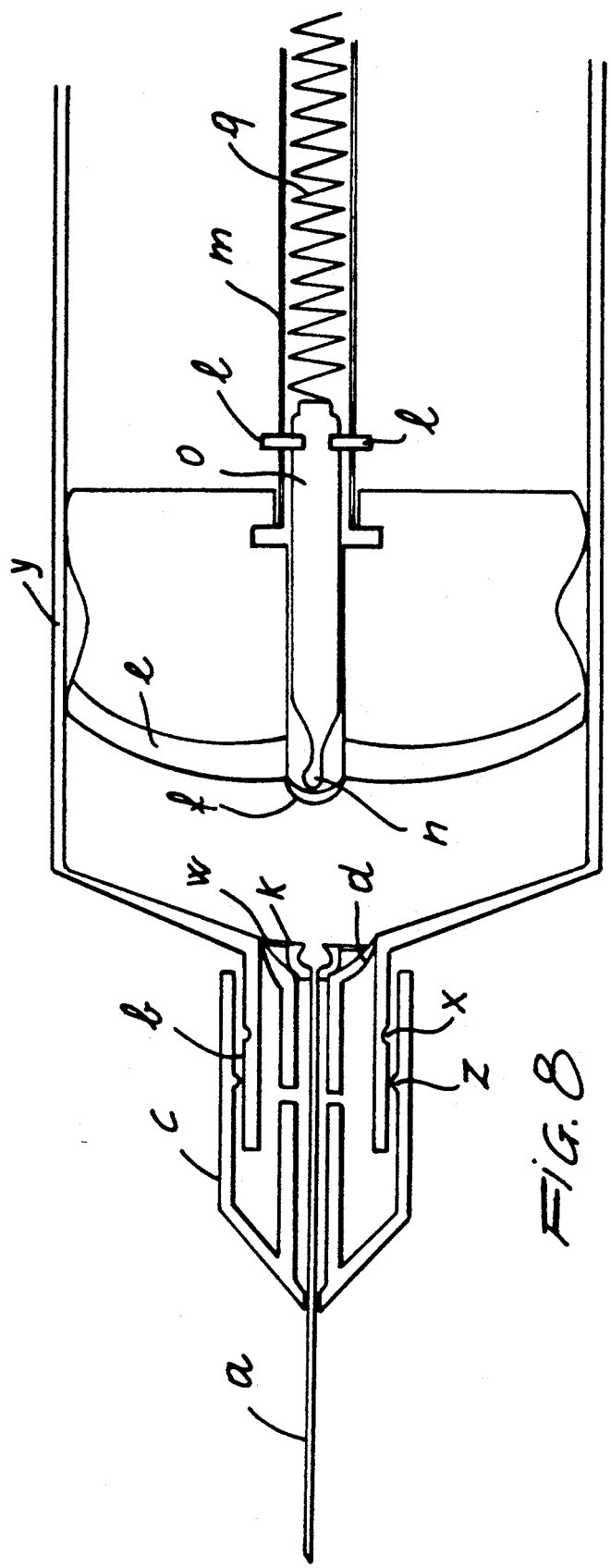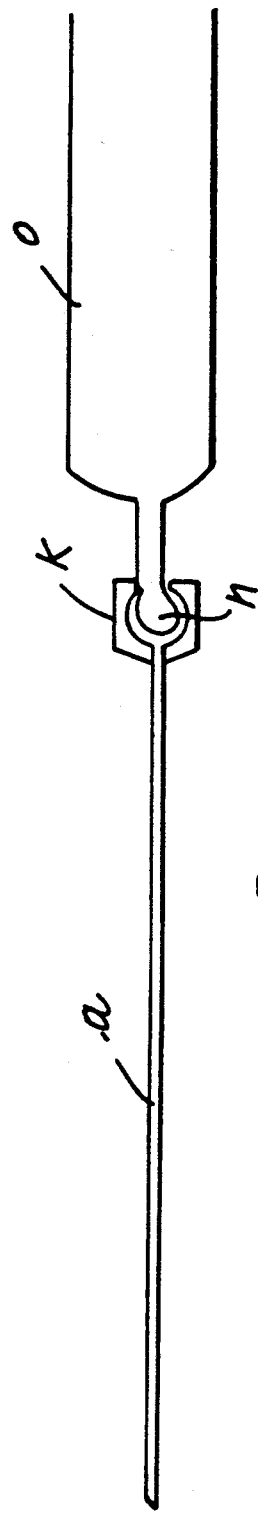

SYRINGE WHICH AUTOMATICALLY MAKE THE HYPODERMIC NEEDLE HARMLESS AFTER USE

This invention concerns a mechanism incorporated with a piston for syringes, which automatically renders the hypodermic needle harmless after use, said mechanism neutralizes the danger and automatically makes the hypodermic syringes equipped with such non-reusable.

The syringes currently on the market improperly defined as monouse have but one single weak protection against accidental injury and may be used, in spite of the written warning "use only once" as many times as desired.

The cap even if inserted is not sufficient protection, since any accidental cause whatsoever may cause it to come off leaving the needle exposed and able to injure and even the act of putting it on may itself constitute a potential danger and risk of injury.

Some inventions are known which act on the whole syringe and depend upon the user and would be designed in such a way as to protect the needle in a definitive way.

There is one type which, after use, retracts the needle inside the canal by means of the piston, with a maneuver carried out by the operator. This is laborious and in any case, it is not automatic. The needle remains floating inside the canal and cannot injure anyone, as long as no one removes the piston from the cylinder causing it to emerge. There are types involving complicated operations which make the needle disappear and remain enclosed, however always acting or involving and modifying the whole structure of the syringe.

These systems involve a total revolutionizing and complete restructuring of machinery from the industrial point of view, and from the point of view of the user, complicated use and dubious safety.

The essential aim of this invention is, while leaving unchanged the form and use of the traditional syringe, to give to the industry a syringe with only the slightest of added costs and to give to the user the possibility to be able to perform injections as he always has done, with the certainty that his syringe may not accidentally puncture himself or others after use, or that someone else may use it again in any way.

This object is achieved with this invention regarding a syringe formed by a cylindrical body, a piston slidable in said body, a perforated needle, characterized in that said needle is provided with a female hook and in said piston is inserted coaxially a cylindrical container which contains a male hooking pawl with its support structure, operatively connected to a pull helicoidal spring, which is fixed to the same cylindrical container and which is operatively connectable to said female hook to draw back and incorporate said needle in said cylindrical container.

In a preferred embodiment, said syringe comprises a cylindrical container open on both sides, which is inserted coaxially in a housing obtained in the normal rod of said piston and which has a rim on its head capable of being housed in a groove of the cap of said piston, said perforated stiletto, or needle, having a female hook, which is slidably supported through a hermetic seal, in a base and which is connected by shearable means to said cylindrical body, a pull helicoid spring extended housed during phase of use inside said cylindrical container and secured at its bottom by a catch and at the other side attached to the support structure of a pawl, which is secured to said cylindrical container by means of at least one pin of shearable material, said pawl with its support structure being inserted, in the phase of use, between the terminal part of said cylindrical container and a canal obtained inside said cap, said canal being closed by a cover of easily perforable material. The condition of the automatic re-entry of the needle, by means of the pawl, is the last pressure activated pushing the piston against the cylindrical body to completely release the liquid through the same needle. Such operation, which permits that the perforated stiletto, or needle, is incorporated in the syringe, is less dangerous and simpler than that which is carried out by the hygienic agents and user communities, as they now insert the protective cap in order to preserve themselves and others.

Concerning the case of drug addicts who use syringes outdoors, throwing them away wherever they might fall, it is unthinkable that they will throw even a single drop of liquid for which they are so desperate and by injecting themselves up to the last drop, they will certainly activate the mechanism which causes the needle to reentry.

Other advantages of this invention lie in the extreme ease of construction and assembly and the extreme slightness of added costs with respect to the normal syringe; maintaining the identical image and use of the traditional syringe; succeeding in guaranteeing that the needle disappear irrevocably after use such that the syringe will be utilized only one time.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

These advantages and innovative and functional features will be further understood by every technician of the field by the description which follows and with the aid of the attached illustrations of FIGS. 1 to 9, as a practical example which are given by way of illustration only, and thus are not limitative of the present invention, and wherein:

FIGS. 1 to 5 show some components of the syringe according to the present invention;

FIG. 6 shows the syringe ready for use;

FIG. 7 shows the syringe with the needle drawn back;

FIG. 8 represents an enlarged detail with the perforated needle in use and the piston almost at the end of its stroke and FIG. 9 represents the moment of hooking between the pawl and the perforated needle.

DETAILED DESCRIPTION OF THE PREFERRED EMBODIMENTS

In the figures, the letter (a) represents the perforated stiletto, or needle and (k) the female hook; (c) represents the base of the perforated stiletto, (b) is the neck of the syringe and (d) is the hermetically sealed gasket, as best shown in FIG. 8. The letter (w) is a membrane of suitable plastic material which fixes the needle (a) to the cylindrical body (u) and is shearable with a predetermined pull force.

The letter (e) represents the cap of the piston rod (v) with the easily perforable cover (f) on the cap head at the center. The cap (e) is an especially resilient (springy) material. Letter (g) is the hole or canal to house the hooking pawl (n) and (h) is the groove to insert the rim (i) of the cylindrical container (m).

The cylindrical container (m) is long enough so as to be inserted in the piston rod (v) and to emerge so as to be able to be inserted stably by means of the rim (i) in the groove (h) of the cap (e). The cylindrical container (m) will have in its walls two holes to house the two pins (l) in easily shearable material, inserted in special notches (p) of the support structure (o) to fix it to the same container (m).

The letter (n) represents the male hooking pawl integral with the support structure (o); (q) is the helicoid pull spring attached to the support structure (o) of the pawl (n) and to the catch (r).

Some catches (z, x) are placed inside the base (c) and outside the neck (b) of cylindrical body (u), as shown in FIG. 2, and are capable of maintaining the base (c) stable and of keeping the needle (a) and its hook (k) at the right distance.

The pawl (n) will be capable of emerging (being discharged) in the center of the cap, lacerating the thin layer of watertight but perforable material (f) covering the hole (g) suitable for exposing it with the last pressure placed on the piston rod (v), thanks to the resilience or elasticity of the head (e) of the cap, so as to discharge all the liquid and at the same time hooking itself, permanently in the hollow protuberance (k) of the perforated stiletto or needle (a).

When the plastic membrane (w) is broken, perforated metallic stiletto, or needle, (a) can slide in its base (c) and in the watertight seal gasket (d) joined or soldered to the base (c) and inserted inside the neck (b) of the hypodermic syringe.

This last above-mentioned pressure will cause the pins to cut the perforable material (l) inserted to jointly hold the cylindrical container (m) with the support casing (o) of the hooking pawl (n) attached to the helicoidal spring (q) in tension, since it is held at the opposite end of the catch (r) to the cylindrical container (m).

The spring (q), once released, while breaking the plastic membrane (w), will close drawing up inside the cylindrical container (m) the support casing (o) of the hooking pawl (n) which at the same time will be inserted in the hollow part (k) of the perforated stiletto (a) consequentially pulling also itself inside the cylindrical container (m) and leaving it permanently harmless and non-reusable. In practice, the details of execution may in any case vary in equivalent manner, in form, arrangement or order of the sections or elements, nature of materials used, without however leaving the innovative concept adopted and therefore keeping within the limits of the invention.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A syringe for automatically rendering a hypodermic needle harmless, the syringe comprising:

a generally cylindrical body having front and rear ends;

a perforated needle extending through the front side of the cylindrical body, the needle being provided with a female hook at one end thereof, the needle being movable only in a direction away from the front end of the cylindrical body after the needle is mounted in the cylindrical body;

a piston slidable in said body toward and away from the needle;

a generally cylindrical container positioned within said piston and being generally coaxial therewith, the cylindrical container having first and second ends;

a cap covering the first end of said cylindrical container, said cap having a canal therein;

a support structure with a male hooking pawl initially located within the cylindrical container at the first end thereof, the male hooking pawl being positionable within the canal of the cap;

a spring positioned within the cylindrical container, the spring being connected between the support structure and the second end of the cylindrical container; and a perforable cover on the cap initially closing the canal, the perforable cover being ruptured by the male hooking pawl when the piston reaches an end of a stroke toward the needle, the male hooking pawl thereby being exposed and engaging the female hook of the needle whereafter the spring automatically pulls the support structure and needle toward the second end of the cylindrical container to completely enclose the needle within the syringe.

2. The syringe according to claim 1, wherein the perforated needle is a stiletto and further comprising a base with a hermetic seal for mounting the stiletto to the cylindrical body.

3. The syringe according to claim 1, wherein the cylindrical container is open on both ends thereof, the cap covering the first end thereof, the syringe further comprises a catch covering the second end of the cylindrical container, the spring being attached to the catch.

4. The syringe according to claim 3, further comprising at least one pin of shearable material, the at least one pin securing the support structure to the cylindrical container, the at least one pin being inserted in a notch on the support structure and being shorn by pressure acting on the piston toward the end of the stroke such that the support structure is free to move whereby the male hooking pawl ruptures the perforable cover and then engages the female hook whereafter the spring pulls the support structure toward the second end of the cylindrical container.

5. The syringe according to claim 4, further comprising a base at the front end of the cylindrical body, the base having a hermetic seal and the needle initially extending through the base and hermetic seal, the syringe further comprising shearable means at the front end of the cylindrical body for initially holding the needle in position, the shearable means being broken when the male hooking pawl engages the female hook to permit the needle to be withdrawn into the syringe.

6. The syringe according to claim 1, further comprising at least one pin of shearable material, the at least one pin securing the support structure to the cylindrical container, the at least one pin being inserted in a notch on the support structure and being shorn by pressure acting on the piston toward the end of the stroke such that the support structure is free to move whereby the male hooking pawl ruptures the perforable cover and then engages the female hook whereafter the spring pulls the support structure toward the second end of the cylindrical container.

7. The syringe according to claim 6, further comprising a base at the front end of the cylindrical body, the base having a hermetic seal and the needle initially extending through the base and hermetic seal, the syringe further comprising shearable means at the front end of the cylindrical body for initially holding the needle in position, the shearable means being broken when the male hooking pawl engages the female hook to permit the needle to be withdrawn into the syringe.

8. The syringe according to claim 1, further comprising a base at the front end of the cylindrical body, the base having a hermetic seal and the needle initially extending through the base and hermetic seal, the syringe further comprising shearable means at the front end of the cylindrical body for initially holding the needle in position, the shearable means being broken when the male hooking pawl engages the female hook to permit the needle to be withdrawn into the syringe.

9. The syringe according to claim 1, wherein the cylindrical container has a rim surrounding the first end thereof and the cap has a groove defined therein, the groove of the cap being insertable on the rim to thereby mount the cap to the cylindrical container.

10. The syringe according to claim 9, wherein the cap is a resilient material and wherein the piston at the end of the stroke will engage the cap with the front end of the cylindrical body.

11. The syringe according to claim 1, wherein the male hooking pawl fails to be exposed to fluid contained when the cylindrical body until the perforable cover is ruptured.

* * * * *